(12) United States Patent
Salamone et al.

(10) Patent No.: US 8,263,720 B1
(45) Date of Patent: Sep. 11, 2012

(54) SACRIFICIAL ADHESIVE COATINGS

(75) Inventors: Joseph Salamone, San Antonio, TX (US); Ann Beal Salamone, San Antonio, TX (US); Xiang Yu, Los Angeles, CA (US); Levi J. Irwin, Alexandria, VA (US)

(73) Assignee: Rochal Industries, LLP, San Antonio, TX (US)

( * ) Notice: Subject to any disclaimer, the term of this patent is extended or adjusted under 35 U.S.C. 154(b) by 0 days.

(21) Appl. No.: 13/253,348

(22) Filed: Oct. 5, 2011

(51) Int. Cl.
*C08F 30/08* (2006.01)
*A61F 13/00* (2006.01)
*C08L 15/00* (2006.01)

(52) U.S. Cl. .......... 526/279; 602/52; 424/443; 523/111; 523/118

(58) Field of Classification Search ............. 602/52
See application file for complete search history.

(56) References Cited

U.S. PATENT DOCUMENTS

| | | | |
|---|---|---|---|
| 3,220,960 A | | 11/1965 | Wichterle et al. |
| 4,062,451 A | * | 12/1977 | Gander ............... 206/524.2 |
| 4,140,115 A | * | 2/1979 | Schonfeld ............... 602/54 |
| 4,525,563 A | * | 6/1985 | Shibata et al. ............ 526/279 |
| 4,743,667 A | * | 5/1988 | Mizutani et al. ............ 526/245 |
| 4,987,893 A | * | 1/1991 | Salamone et al. ............ 602/52 |
| 5,103,812 A | * | 4/1992 | Salamone et al. ............ 602/52 |
| 5,376,378 A | * | 12/1994 | Li et al. ............... 424/448 |
| 5,667,771 A | * | 9/1997 | Carballada et al. ......... 424/70.12 |
| 6,022,330 A | * | 2/2000 | Chen et al. ............... 602/8 |
| 6,358,503 B1 | * | 3/2002 | Gerrish ............... 424/78.03 |
| 6,383,502 B1 | * | 5/2002 | Dunshee et al. ............ 424/401 |
| 7,267,681 B2 | * | 9/2007 | Dunshee ............ 606/214 |
| 7,318,937 B2 | * | 1/2008 | Jonn et al. ............ 424/487 |
| 7,344,731 B2 | | 3/2008 | Lai et al. |
| 7,641,893 B2 | * | 1/2010 | Salamone et al. ............ 424/78.31 |
| 7,795,326 B2 | * | 9/2010 | Salamone et al. ............ 523/118 |
| 7,884,141 B2 | * | 2/2011 | Salamone et al. ............ 523/106 |
| 2008/0137030 A1 | | 6/2008 | Hoffman |
| 2009/0192275 A1 | | 7/2009 | Salamone et al. |
| 2009/0258058 A1 | * | 10/2009 | Thomas et al. ............ 424/445 |
| 2011/0086077 A1 | | 4/2011 | McCrea et al. |

OTHER PUBLICATIONS

Wichterle et al., "Hydrophilic Gels for Biological Use", Nature 185, 117-118; Jan. 9, 1960.
Bolton, "Evidence-based Report Card: Operational Definition of moist wound healing", J. Wound Ostomy & Continence Nursing, 2007, 34(1):23-29.

* cited by examiner

*Primary Examiner* — Robert S Loewe
(74) *Attorney, Agent, or Firm* — Duane Morris, LLP; J. Rodman Steele, Jr.; Gregory M. Lefkowitz

(57) ABSTRACT

Combinations of solubilized, covalently crosslinked, siloxy-containing polymers in a solvent system of a volatile hydrophobic (non-polar) liquid that is non-stinging to a user are excellent non-irritating liquid coating materials for forming films, which, after solvent evaporation, are water insoluble but water-vapor permeable and lightly adherent to surfaces such as skin and mucous membranes. The crosslinking content is greater than 1 weight % and can be as much as 16 weight %. In comparison to non-crosslinked polysiloxy films, or crosslinked films of 1 weight % or less, the enhanced crosslinked polysiloxy films, while continuing to be soluble in the solvent, have reduced tack and reduced adhesion to skin and can act as sacrificial coatings under strongly adherent pressure sensitive adhesives.

26 Claims, No Drawings

SACRIFICIAL ADHESIVE COATINGS

FIELD OF INVENTION

This invention relates generally to highly covalently crosslinked, yet solvent-soluble, liquid adhesive coatings that, after solvent evaporation, are useful for protecting surfaces, including skin and mucous membranes, by acting as water-insoluble, water-vapor permeable, adhesive, sacrificial coatings.

BACKGROUND OF THE INVENTION

Liquid adhesive bandages prepared from siloxy-containing hydrophobic polymers admixed with volatile liquid polydimethylsiloxanes and volatile liquid alkanes (U.S. Pat. No. 4,987,893, U.S. Pat. No. 5,103,812, the entirety of which is incorporated herein by reference, and U.S. Pat. No. 6,383,502) have been reported to provide non-stinging, non-irritating liquid bandage coating materials after solvent evaporation that allow body fluid evaporation while protecting the body surface from further contamination and desiccation. No indication of covalent crosslinking of the siloxy-containing hydrophobic polymers was taught in these patents.

Additionally, amphiphilic siloxy-containing polymers have also been reported as liquid adhesive bandages (U.S. Pat. No. 7,795,326, the entirety of which is incorporated herein by reference), wherein the hydrophobic siloxysilane monomer is copolymerized with a hydrophilic nitrogen-containing monomer.

The preferred siloxy-containing monomer for both the hydrophobic and amphiphilic liquid adhesive bandages of the above mentioned patents is based upon the siloxy monomer, 3-methacryloyloxypropyltris(trimethylsiloxy)silane (TRIS).

In U.S. Pat. No. 7,795,326, it was reported that siloxy-containing monomers may also contain low concentrations of siloxysilane crosslinking agents. These crosslinking agents could be dimeric or higher in their polymerizable groups. For example, the commercial TRIS monomer often contains minor amounts of the TRIS dimer of 1,3-bis(3-methacryloyloxypropyl)-1,1,3,3-tetrakis(trimethylsiloxy)disiloxane, which was reported to increase the strength of the coating polymer. Additionally, in U.S. Pat. No. 7,795,326 it was stated that siloxy monomer combinations containing siloxysilane crosslinking agents may be utilized provided that the resulting polymer solubility is not compromised in the volatile, hydrophobic solvent. It is taught that when the hydrophobic siloxy-containing monomer is TRIS, low concentrations of crosslinking was preferably less than 1.0 weight % of TRIS dimer, more preferably between 0.5-0.8 weight %, and most preferably between 0-0.15 weight %. Thus, in a copolymerization with other monomers, the overall dimer content in the comonomer formulation would be reduced further relative to the concentration of the added comonomers.

In general, for free radically crosslinked polymers in a compatible solvent, gelation often occurs at a crosslinking content of less than 1 weight %. In U.S. Pat. No. 3,220,960 it is taught that in copolymerization of a monomer having a polymerizable group with a small amount of a monomer having two such groups in organic solvent solution, a gel is formed by the crosslinked corresponding polymer and the solvent. Utilizing this principle, hydrogel contact lenses are reported to be made from hydrophilic esters of acrylic and methacrylic acid with a small amount of a diester of these polymerizable acids, wherein the diester preferably does not amount to more than one percent of the monomer. In such a system the original soft, 38% water, hydrogel contact lens, poly(2-hydroxyethyl methacrylate), was based upon the polymerization of the hydrophilic monomer 2-hydroxyethyl methacrylate (HEMA) crosslinked with a small amount of ethylene glycol dimethacrylate (Wichterle, O.; Lim, D., Nature, 1960, 185, 117-118), a crosslinking agent with a similar radical reactivity to that of the HEMA monomer.

Crosslinking of contact lenses with multivalent monomers is known in the contact lens industry to produce stable, insoluble materials. For example, in U.S. Pat. Nos. 7,344,731 and 7,884,141, and US Patent Application Publication Nos. 2008/0137030 and 2009/0192275, TRIS dimer has been used to produce insoluble contact lenses with a variety of other monomers. However, none of these references relates to liquid coating materials and, in direct contrast to the properties of the inventive polymers and coating materials, each of these references requires that the contact lenses are insoluble in order to maintain their function.

For pressure sensitive adhesives applied to the skin, pain usually results during dressing removal when the epidermis is damaged or when the hair is pulled by the adhesive. A strong adhesive on wounded or inflamed skin is not desired because of increased damage to the skin and a resulting delay in healing.

In the utilization of sacrificial skin coatings, adhesive failure of the coating to the skin is preferred, as opposed to the adhesive removing a portion of the epidermis, hair, or scar tissue when it is removed from the body. In the case of adhesive failure, preferably the adhesive fails at the adhesive/substrate interface, leaving little or no residue. Thus, when a stronger, more adherent pressure sensitive adhesive is applied over the sacrificial adhesive, the more tenacious adhesive removes the weaker adhesive from the skin, giving a painless (or reduced pain) removal process.

Silicone pressure sensitive adhesives and silicone gel adhesives, which are often in two part kits causing crosslinking in situ, are generally considered the most comfortable adhesives for painless removal from the skin. These are generally first applied to a backing material, crosslinked in place, and then applied to the skin. They have a disadvantage in not being applied as a liquid adhesive bandage, which limits their ability to intimately conform to a contoured skin surface or a wounded, damaged or inflamed skin surface as would a liquid adhesive bandage, which permits the polymer solution to flow into crevices and skin folds.

In US Patent Application Number 2011/0086077, highly crosslinked silicone hydrogels are discussed as tissue adhesives for wound repair, wherein silicone monomers and crosslinking agents can be applied as a wound dressing, either as a film or as an aqueous emulsion monomer solution placed upon the wound, followed by polymerization and crosslinking directly upon the wound. Such a process requires activation of polymerization, which can generate heat upon the wound when monomers polymerize. Initiation of polymerization utilizes a monomer mix containing either addition type vinyl monomers or condensation type monomers directly upon a tissue. In addition to heat being generated upon the wound or bodily surface, this is a polymerization in situ and residual monomer is often present because of incomplete polymerization. Such residual monomer upon a skin or wound surface often leads to allergic responses. Additionally, water is the preferred solvent as an oil-in-water emulsion for this polymerization, which would lead to slow drying on the skin because of the high heat of volatilization of water. Furthermore, addition of a pressure sensitive adhesive over such a formulation could be difficult if water remains in the silicone hydrogel.

Thus, there is a need in the art to provide a water-insoluble, intimately conformable, water-vapor permeable, adhesive polymer film delivered from a volatile non-stinging solvent which, after solvent evaporation, forms a polymer coating that protects the skin and wounds and acts as a sacrificial coating that can be used under strongly adherent tapes and adherent medical devices in order to reduce trauma to the underlying skin upon removal of the tape or medical device.

SUMMARY

Surprisingly, it has been found in this invention that when the level of covalent crosslinking of siloxy-containing polymers in volatile, non-stinging solvents by siloxy crosslinking monomers is substantially greater than that reported in U.S. Pat. No. 7,795,326, i.e., greater than 1 weight % to about 16 weight %, solubility and flowability in the volatile solvent are maintained and the adhesive strength of the resulting polymer coating is greatly diminished after solvent evaporation. It is indeed unexpected that a highly crosslinked siloxy-containing polymer could be soluble in a solvent, that a smooth film could be adhered to the skin, and that the crosslinked polymer film is less adhesive than a corresponding non-crosslinked siloxy-containing polymer, or low crosslinked siloxy-containing polymer of U.S. Pat. No. 7,795,326. This behavior is thus contrary to that suggested by U.S. Pat. No. 7,795,326. Because of the unexpected solubility phenomenon, highly crosslinked siloxy-containing polymers in volatile, non-stinging solvents can be used as sacrificial coatings under pressure sensitive adhesives of higher adhesive strength.

This invention pertains to soluble, crosslinked siloxy-containing polymers and their inclusion in liquid adhesive materials that can be used as sacrificial coatings under more adherent materials for protecting surfaces, such as of a biological origin, including skin and mucous membranes. The polymer component of the liquid adhesive material comprises an ethylenically unsaturated addition polymerizable monomer containing at least one siloxysilane and at least one ethylenically unsaturated addition polymerizable siloxy crosslinking monomer. The concentration of the crosslinking siloxy monomer is greater than 1 weight % to 16 weight % of the polymerizable siloxysilane non-crosslinking monomer, in combination with other ethylenically unsaturated addition polymerizable monomers, if desired. Other monomers or additives may contribute hardness, softness, elasticity, hydrophobicity, hydrophilicity, increased adhesion or decreased adhesion of the sacrificial polymer coatings.

The sacrificial adhesive bandage coatings of this invention are based upon a weakly adhesive liquid bandage that forms a clear adhesive coating on the skin and, when covered by a more adhesive system, is removed without damaging the skin when the strongly adhering adhesive covering is removed; that is, it is sacrificed instead of causing dermal damage or trauma. An example of this technology would be the application of an ostomy device, wherein the pressure sensitive adhesive on the ostomy device is adhered to the skin surrounding a stoma. As the ostomy device is filled with body fluids, it must be removed and discarded, and replaced by a new device containing a new adhesive. The removal of the ostomy device can be painful because of the removal of a portion of the patient's epidermis, in addition to the patient's hair or scar tissue formation. A sacrificial bandage coating would function by being an interface between the pressure sensitive adhesive of the ostomy device and the surface of the skin to which the device is attached.

As another example of the use of a sacrificial bandage coating, when an intravenous needle is used in a patient, the needle and tubing are held in place by a strongly adherent pressure sensitive adhesive surgical tape to keep the device secure from movement. When the surgical tape is removed from the device, pain is experienced by the patient as a portion of the skin and hair are removed. Thus, if an adhesive conformal sacrificial coating were first placed upon the skin, followed by the strongly adhesive tape, pain would be greatly reduced.

The crosslinked siloxy polymers dissolve when incorporated into volatile liquid siloxanes or volatile alkanes and appear homogeneous to the human eye and flow freely without the appearance of lumps or particulate matter. This polymer-containing solution provides for a fast drying, flexible, waterproof, breathable, non-stinging, lightly adhesive coating, which functions as a sacrificial skin-protecting coating when used under a more adherent adhesive.

In a preferred embodiment, the siloxy dimer content is from 1 weight (wt) % to 16 weight % or between 2 and 10 weight %, or between 3 and 8 weight %, or between 4 and 7 weight %, based on the weight of the crosslinked siloxy polymer.

The polymers can be prepared from the polymerization of the respective monomers in a 30 weight % concentrated solution. Such concentrated conditions normally facilitate gelation with crosslinking monomers. However, the results obtained are surprising and unexpected in that highly crosslinked polymer systems with crosslinking contents greater than 1 weight % and up to 16 weight % are soluble in solution and free-flowing. Polymer solutions cast from these solutions are smooth and transparent, suggesting that the polymer sizes are smaller than the wavelength of light. Normally, under such high crosslinking conditions, either insolubility by precipitation or gelation of the resulting polymer occurs, yielding materials that cannot be utilized as soluble and spreadable liquid adhesive bandages. Additionally, many of the cast polymer films appeared to be soft, ductile and/or elastic, which is not anticipated for highly crosslinked polymer films in the solid state.

The sacrificial adhesive coating may contain medicants or other active materials that may be released over time onto targeted areas, if desired.

The liquid polymer-containing coating materials of this invention comprise a covalently crosslinked siloxysiloxane-containing polymer and a solvent system comprising a volatile liquid that is non-stinging and non-irritating to a user, but provides bulk and formability to the liquid. Preferably, the polymer is present from 1 to 50% by weight of the coating material, of which a crosslinking monomer is incorporated from greater than 1 to 16 weight % based upon the total polymer concentration, and the volatile liquid from 50 to 99% by weight of the coating material. The solvent is minimized to facilitate spreading of the sacrificial liquid adhesive coating within a desired area. The material forms a sacrificial coating or bandage in the form of a dried, transparent, lightly adhesive film when applied to a surface or the skin of a user.

Preferably, the siloxane containing polymer comprises at least one vinyl containing alkylsiloxysilane monomer and preferably comprises an addition polymerizable comonomer. The volatile liquid is a low molecular weight polydimethylsiloxane, such as hexamethyldisiloxane or octamethyltrisiloxane; a low molecular weight cyclic siloxane, such as hexamethylcyclotrisiloxane or octamethylcyclotetrasiloxane; a linear, branched or cyclic alkane, such as propane, butane, and isobutane (under pressure), pentane, hexane, heptane, octane, isooctane, petroleum distillates, or cyclohexane; a chlorofluorocarbon such as trichloromonofluoromethane, dichlorodifluoromethane, and dichlorotetrafluoroethane; a fluorocarbon such as tetrafluoroethane, heptafluoropropane, 1,1-difluoroethane, pentafluoropropane, perfluoroheptane, perfluoromethylcyclohexane, hydrofluoroalkanes such as 1,1,1,2,-tetrafluoroethane and 1,1,1,2,3,3,3-heptafluoropropane, combinations thereof and the like; a volatile gas under pressure, such as liquid carbon dioxide; or a mixture thereof. As will be understood, when stored under high pressure, carbon dioxide can be present in the form of a liquid at room temperature. The volatile solvent can be hexamethyldisiloxane, isooctane, and mixtures thereof. The volatile solvent can be hexamethyldisiloxane.

More polar solvents such as ethanol, isopropanol, acetone, glycerin, propylene glycol, N-methylpyrrolidone, and N,N-dimethylacetamide can be added in small amounts (10 weight % or less) to enhance polymer solubility, but these solvents should not interfere with the overall solvent composition being non-stinging to a user.

It is a feature of the invention that the liquid materials can be applied over a temperature range of −10° C. to +45° C. when applied to skin, nails, or mucous membranes of a user to form films that are excellent sacrificial coatings in minutes. In particular, it is a property of the liquid coating materials that once the coating material is applied at room temperature, the adherent coating can form in less than 5 minutes, less than 3 minutes, less than 2 minutes, less than 1 minute, less than 30 seconds or less than 15 seconds.

These coatings are not a nutrient source for microorganisms, are conformable, comfortable and can be elastic and flexible. The films do not irritate the skin and mucous membranes when sprayed or deposited in any way during application and in use after drying. The dried coatings formed are substantially waterproof, yet have high water vapor and oxygen gas transmission. The coatings are formed rapidly at standard room temperature (i.e., approximately 25° C. or 77° F.).

The liquid composition and/or dried polymer film can have various medicaments or other agents incorporated therein for maintaining sterility and/or for release to the underlying area of the body of a user. Such polymer films can function as transdermal drug release coatings as well as function in a controlled release fashion to the skin. For example, the dried polymer films can contain solid, suspended antibacterial agents, antiviral agents, antifungal agents, antiprotozoal agents, antibiotics, anti-inflammatory agents, anti-allergic agents, anti-infective agents, antiparasitic agents, antiperspirant agents, wound healing agents, anti-VEGF agents, anti-psoriasis agents, disinfectants, anti-itching agents, anesthetic agents, dermatological agents, anti-androgenic agents, anti-acne agents, anti-aging agents, anti-parasitic agents, anti-depressant agents, steroids, and non-steroidal anti-inflammatory drugs or similar materials, which can be released from the sacrificial coatings to the underlying skin.

The invention is also drawn to a method of coating a surface by applying one of the liquid, polymer-containing coating materials described herein to a surface in order to form a coating. The surface can be skin. The method can also include applying an adhesive and/or a medical device over the coating, i.e., using the coating as a sacrificial coating.

The invention is also drawn to the soluble, crosslinked siloxy-containing polymer component of the liquid, polymer-containing coating materials described herein. The soluble, crosslinked siloxy-containing polymer can include 34 to 99 monomer-weight-% of at least one polymerizable siloxy-containing monomer component, and greater than 1 to 16 monomer-weight-% siloxy-containing crosslinking agent. Of particular importance, contrary to highly crosslinked siloxy-containing polymers known in the art, the highly crosslinked siloxy-containing polymers described herein have a solubility limit in HMDS, isooctane or both that is at least 5 wt-%. The highly crosslinked siloxy-containing polymers can have any of the compositions described herein for the polymer component of the liquid, polymer-containing coating materials.

It is an object of the invention to provide liquid adhesive bandage materials that, after solvent evaporation, are useful for protecting biological surfaces, including skin and mucous membranes, by acting as sacrificial coatings.

In another aspect of the invention, liquid adhesive bandage materials are provided that are useful for protecting biological surfaces and form conformal, adhesive films after solvent evaporation.

In another aspect, the polymer, when incorporated into volatile non-polar liquids, provides for a fast drying, adherent, flexible, breathable, water-insoluble, water vapor permeable, oxygen permeable, non-stinging, sacrificial, liquid adhesive coating or bandage.

In another aspect, the sacrificial adhesive coating contains therapeutic molecules or other active ingredients that may be gradually released onto targeted areas.

It is an object of the invention to provide siloxysiloxane-containing polymers with greater than 1 weight % crosslinking monomer to the skin that are less adhesive than related siloxane-containing polymers containing less than 1 weight % crosslinking monomer.

It is a further object to provide crosslinked siloxane-containing polymers in a volatile, non-stinging, non-irritating solvent that appear homogeneous to the human eye.

It is a further object to provide crosslinked siloxane-containing polymers in a volatile, non-stinging, non-irritating solvent that is free-flowing.

It is a further object to provide crosslinked siloxane-containing polymers in a volatile, non-stinging, non-irritating solvent that can be cast upon the skin or mucous membranes, followed by solvent evaporation.

It is a further object to provide crosslinked siloxane-containing polymers in a volatile, non-stinging, non-irritating solvent that, after solvent evaporation, form transparent, non-lumpy, smooth films.

It is a further object of this invention to solvate the crosslinked siloxane-containing polymers in a volatile, non-stinging solvent of linear and cyclic siloxanes, linear, branched and cyclic alkanes, volatile fluorocarbons, volatile chlorofluorocarbons, and mixtures thereof.

It is a further object of this invention to solvate the crosslinked siloxane-containing polymers in liquid carbon dioxide.

It is a further object of the invention to provide a low adhesive polymer-containing coating that can be applied to the skin or mucous membranes from solvation in and evaporation of a volatile, non-stinging, non-irritating solvent.

It is a further object of the invention to provide a non-tacky, transparent or translucent coating that does not attract or hold dirt and can remain colorless and clear for wound viewing as well as cosmetic attractiveness.

It is a further object of the invention to provide a sacrificial coating on skin under an ostomy adhesive.

It is a further object of the invention to provide a sacrificial coating on skin for adhesive trauma protection, including negative pressure wound therapy.

It is a further object of the invention to provide a sacrificial coating for periwound skin protection.

It is a further object of the invention to provide a sacrificial coating for peritube skin protection.

It is a further object of the invention to provide a sacrificial coating for protection at intravenous sites.

It is a further object of the invention to provide a sacrificial coating from adhesive trauma from endotracheal tubes.

It is a further object of the invention to provide a sacrificial coating from adhesive trauma from maceration around tracheostomy tubes.

It is a further object of the invention to provide a sacrificial coating from adhesive trauma at infusion sites.

It is a further object of the invention to provide a sacrificial coating from adhesive trauma from condom catheters.

It is a further object of the invention to provide a sacrificial coating under an adherent medical device.

In another aspect, a transparent coating is provided that reduces pain and inflammation when applied to damaged or irritated skin or tissue.

In another aspect, a coating is provided that remains adherent to a surface when exposed to external water, soaps, detergents, and most skincare products.

In another aspect, a coating is provided that remains adherent to a surface when exposed to varying external humidity and temperature conditions.

In another aspect, a coating is provided that is adherent under flex stress, including bending, twisting, and stretching.

In another aspect, a coating is provided that prevents exogenous microorganism or particulate contamination to skin or mucous membrane wounds or incisions.

In another aspect, a coating is provided which, when applied, controls body fluid loss from an abraded area.

It is a further object of this invention to provide a coating that is water insoluble but is water vapor permeable.

It is a further object of this invention to provide a coating that is oxygen permeable.

It is a further object of the invention to provide a low surface tension polymer solution that will flow readily into confined spaces.

It is a further object of the invention to provide a coating that, after application to a surface and in the absence of a covering pressure sensitive adhesive, releases from that surface gradually over time without requiring externally applied solvents or other removal methods.

It is a further object of the invention to provide an adhesive coating between two similar or different substrates that can be easily removed.

DETAILED DESCRIPTION

Soluble, crosslinked siloxy-containing polymers and liquid coating materials containing the same, as well as, methods of using the coating materials are described herein. The crosslinked siloxy-containing polymers can include 34 to 99 monomer-weight-% of at least one polymerizable siloxy-containing monomer component, and greater than 1 to 16 monomer-weight-% siloxy-containing crosslinking agent. Contrary to known highly crosslinked siloxy-containing polymers, the highly crosslinked siloxy-containing polymers described herein have a solubility limit in hexamethyldisiloxane (HMDS), isooctane or both of at least 5 wt-%. The highly crosslinked siloxy-containing polymers can have any of the compositions described herein for the polymer component of the liquid, polymer-containing coating materials. The coating materials can include about 1 to 50 weight % of the crosslinked siloxy-containing polymer and about 50 to 99 weight % of a non-stinging, volatile, hydrophobic liquid as part of a solvent system, where the crosslinked siloxy-containing polymer is solubilized in the solvent system.

Polymerizable siloxy-containing monomer components useful in the crosslinked siloxy-containing polymer of the present invention include siloxysilanes that may be water vapor and oxygen permeable. Polymerizable siloxysiloxanes that may be reacted individually with a crosslinking agent and with other monounsaturated monomers to form copolymers, terpolymers, multi-polymers, graft polymers, block polymers, branched polymers, star polymers, or dendritic polymers include, but are not limited to:

3-methacryloyloxypropyltris(trimethylsiloxy)silane (TRIS),
3-methacryloyloxypropylpentamethyldisiloxane,
3-methacryloyloxypropylbis(trimethylsiloxy)methylsilane,
3-methacryloyloxypropyltris(vinyldimethylsiloxy)silane,
3-methacryloyloxynnethylbis(trimethylsiloxy)(pentamethyldisiloxanyl)silane-,
3-methacryloyloxyethyltris(pentamethyldisiloxanyl)silane,
methacryloyloxymethylbis(trimethylsiloxy)methylsilane,
methacryloyloxymethyltris(trimethylsiloxy)silane,
3-methacryloyloxypropyl heptacyclopentyl-T8-silsesquioxane,
3-methacryloyloxypropylheptaisobutyl-T8-silsesquioxane,
3-acryloyloxypropylmethylbis(trimethylsiloxy)silane,
3-acryloyloxypropyltris(trimethylsiloxy)silane,
3-acryloyloxypropylpentamethyldisiloxane,
3-methacryloyloxypropyl-1,1,1-triphenyl-3,3-dimethyldisiloxane,
methylbis(trimethylsiloxy)silylpropylglyceryl methacrylate,
tris(trimethylsiloxy)silylpropylglyceryl methacrylate,
methacryloyloxymethylphenethyltris(trimethylsiloxy)silane,
di[(trimethylsiloxy)silylpropyl]itaconate,
3-methacrylamidopropylbis(trimethylsiloxy)methylsilane,
3-methacrylamidopropyltris(trimethylsiloxy)silane,
3-acrylamidopropyltris(trimethylsiloxy)silane,
N-(trimethylsiloxy)silylpropyl maleimide,
p-vinylphenyltris(trimethylsiloxy)silane,
p-vinylbenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentamethyldisiloxane,
O-(vinyloxyethyl)-N-(tris[trimethylsiloxy]silylpropyl)urethane,
vinylphenylbis(trimethylsiloxy)silane,
vinyltris(dimethylsiloxy)silane,
vinyltris(trimethylsiloxy)silane,
allyltris(trimethylsiloxy)silane,
N-tris(trimethylsiloxysilyl)propylmaleimide,
bis(trimethylsiloxy)silylpropyl itaconate,
vinyl-terminated polydimethylsiloxane,
3-(trimethylsilyl)propyl vinyl carbonate,
3-[tris(trimethylsiloxy)silyl]propyl vinyl carbonate,
3-[tris(trimethylsiloxy)silyl]propyl vinyl carbamate,
t-butyldimethylsiloxyethyl vinyl carbonate,
trimethylsilylethyl vinyl carbonate,
trimethylsilylmethyl vinyl carbonate,
polydimethylsiloxane monoacrylate,
polydimethylsiloxane monomethacrylate,
polymethylphenylsiloxane monoacrylate,
polymethylphenylsiloxane monomethacrylate,
monomethacryloxypropyl-terminated polydimethylsiloxanes,
3-acryloyloxypropyltris(polydimethylsiloxanyl)silane,
mono(3-acryloxy-2-hydroxypropoxypropyl)-terminated polydimethylsiloxane, O-methacryloxyethyl-N-(trimethylsiloxysilylpropyl)carbamate,
O-methacryloxyethoxy-N-[bis(trimethylsiloxy)methylsilyl]propylcarbamate,
N-(3-methacryloxy-2-hydroxypropyl)-3-aminopropyltris(trimethylsiloxy)silane,
(3-methacryloxy-2-hydroxypropoxy)propylbis(trimethylsiloxy)methylsilane,
methacryloyloxy(polyethyleneoxy)propyltris(trimethylsiloxy)silane, and the like.

The siloxysilane monomers may make the crosslinked siloxy-containing polymer soluble in the preferred non-polar, non-stinging, volatile solvent systems. Exemplary siloxy-containing monomers include polymerizable alkylsiloxysilanes, arylsiloxysilanes and alkylarylsiloxysilanes, with alkylsiloxysilanes being more preferred. The siloxy-containing monomers can be methacrylated alkylsiloxysilanes, such as 3-methacryloyloxypropyltris(trimethylsiloxy)silane (TRIS).

The siloxy-containing monomer component can be present in an amount ranging from 34 to 99 wt-%, or from 50 to 99 wt-%, or from 60 to 98.75 wt-%, or from 70 to 98.5 wt-% or from 80 to 98.5 wt-% based on the total weight of the crosslinked siloxy-containing polymer. The siloxy-containing monomer component can be at least 50 wt-%, or at least 60 wt-%, or at least 70 wt-%, or at least 80 wt-%, or at least 84 wt-%, or at least 90 wt-% based on the total weight of the crosslinked siloxy-containing polymer.

As used herein, a polymer is "soluble" or "solubilized" if the amount of polymer present in the solvent system is completely dissolved in the solvent system without the polymer forming a precipitate or visible, swollen gel particles in solution. As used herein, the term "solubility limit" is the maximum amount, measured as a percentage of the total weight of the solution, of a given polymer that can be dissolved in a given solvent system. For example, the crosslinked siloxy-containing polymer can have a solubility limit of at least 5 wt-%, at least 10 wt-%, at least 15 wt-%, at least 20 wt-%, at least 25 w, or at least 30 wt-% in the HDMS, isooctane or any other solvent system described herein, based on the total weight of the liquid, polymer-containing coating material.

Other addition polymerizable monomers may also be incorporated into the polymers of this invention to modify adhesion, cohesion, elasticity, flexibility, toughness, transparency, opaqueness, color, fluorescence, ultraviolet absorbance, infrared absorbance, increased or decreased refractive index, oxygen permeability, oxygen solubility, water content, water-vapor permeability, biodegradation, cytotoxicity, crazing, fracturing, density, thermal expansion, creep, compressibility, heat capacity, thermal conductivity, glass transition temperature, and combinations thereof. Typical addition polymerizable comonomers which may be reacted with the vinylalkylsiloxysilanes to form multipolymers are: methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, stearyl acrylate, stearyl methacrylate, benzyl methacrylate, 2-butoxyethyl acrylate, n-butyl acrylate, n-butyl methacrylate, methacrylic anhydride, 2-(methacryloyloxy)ethyl acetoacetate, ethyl acrylate, behenyl methacrylate, ethyl methacrylate, dimethyl itaconate, di-n-butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, α-methylstyrene, styrene, p-t-butylstyrene, 4-methoxystyrene, N-vinylcarbazole, n-octadecyl acrylate, n-octadecyl methacrylate, 2-phenylethyl methacrylate, n-tridecyl methacrylate, vinyl benzoate, vinyl naphthalene, di-isooctyl itaconate, acrylamide, N-methylacrylamide, N-phenylacrylamide, N-ethylacrylamide, N-(hydroxymethyl)acrylamide, N-(hydroxymethyl)methacrylamide, N-[tris(hydroxymethyl)methylacrylamide, N-isopropylacrylamide, N,N-diethylacrylamide, N,N-dimethylacrylamide, N,N-dimethylmethacrylamide, N-diphenylmethylacrylamide, N-(triphenylmethyl)methacrylamide, N-acryloylamidoethoxyethanol, diacetone acrylamide, N-vinylpyrrolidone, N-vinylcaprolactam, N-vinylformamide, N-vinyl-N-methylformamide, N-vinylacetamide, N-vinylphthalamide, N-(2-methacryloyloxyethyl)ethylene urea, N-(2-methacrylamidoethyl)ethylene urea, 4-acryloylmorpholine, maleimide, N-methylmaleimide, N-(2,3-dihydroxypropyl)maleimide, N-vinylsuccinimide, N-vinyldiacetamide, epsilon-acryloyllysine, N-acryloyluracil, N-acryloylthymine, N-acryloyladenine, N-acryloylguanine, N-acryloylurea, N-acryloylguanidine, N-acrylglucosamine, N-allylpyrrolidone, N-allylacetamide, N,N-dimethylaminoethyl methacrylate, N,N-dimethylaminoethyl acrylate, N,N-diethylaminoethyl methacrylate, N,N-diethylaminoethyl acrylate, N,N-dimethylaminopropylmethacrylamide, N,N-dimethylaminopropylacrylamide, vinylbenzyl-N,N-dimethylamine, methacryloyloxyethylamine, N-vinylimidazole, 4(5)-vinylimidazole, 4-vinylpyridine, 2-vinylpyridine, 2-methyl-5-vinylpyridine, vinyltriazine, 4-aminostyrene, p-hydroxystyrene, 2-hydroxyethyl methacrylate, 2-hydroxyethyl acrylate, glyceryl methacrylate, glyceryl acrylate, 4-hydroxybutyl acrylate, poly(ethylene glycol) monoacrylate, poly(ethylene glycol) monomethacrylate, poly(ethylene glycol monomethyl ether) methacrylate, diethylene glycol monoacrylate, diethylene glycol monomethacrylate, triethylene glycol monoacrylate, triethylene glycol monomethacrylate, tetraethylene glycol monoacrylate, tetraethylene glycol monomethacrylate, triethylene glycol methyl ether methacrylate, triphenylmethyl methacrylate, and the like. In addition fluorinated monomeric siloxanes, fluorinated itaconates, fluorinated methacrylates or acrylates, such as hexafluoroisopropyl methacrylate, can be used. Furthermore, in certain instances, acidic monomers such as acrylic acid, methacrylic acid, itaconic acid, fumaric acid, β-carboxyethyl acrylate, mono-2-(methacryloyloxy)ethyl maleate, mono-2-(methacryloyloxy)ethyl succinate, 2-acetamidoacrylic acid, 2-acrylamidoglycolic acid, 2-acrylamido-2-methyl-1-propanesulfonic acid and its salts, and vinylbenzoic acid can be used, particularly to coordinate with cationic, biologically active compounds. Alternatively, cationic monomers can be added to increase adhesion to anionic surfaces, which include (3-acrylamidopropyl)trimethylammonium chloride, [3-(methacryloylamino)propyl]trimethylammonium chloride, (3-methacryloyloxyethyl)trimethylammonium chloride and vinylbenzyltrimethylammonium chloride, and related salts. Zwitterionic monomers such as [3-(methacryloylamino)propyl]dimethyl(3-sulfopropyl)ammonium hydroxide inner salt and [2-(methacryloyloxy)ethyl]dimethyl-(3-sulfopropyl) ammonium hydroxide inner salt can also be added. The addition polymerizable monomers may be present in the crosslinked siloxy-containing polymer in an amount ranging from 3 to 60 wt-%, or from 10 to 55 wt-%, or from 20 to 50 wt-%, or from 30 to 48 wt-% or from 35 to 47.5 wt-% based on the total weight of the crosslinked siloxy-containing polymer. The addition polymerizable monomer component can be at least 10 wt-%, or at least 20 wt-%, or at least 30 wt-%, or at least 40 wt-%, or at least 46.4 wt-%, or at least 60 wt-% based on the total weight of the crosslinked siloxy-containing polymer.

Preferred polymerizable comonomers include methyl methacrylate, N-isopropylacrylamide, dimethyl itaconate, n-dibutyl itaconate, 2-ethylhexyl acrylate, isooctyl acrylate, N-vinylpyrrolidone, N,N-dimethylaminopropylacrylamide, and N,N-dimethylaminoethyl methacrylate and combinations thereof, with methyl methacrylate, isooctyl acrylate, and N-isopropylacrylamide being more preferred, and methyl methacrylate being most preferred.

In certain instances, particularly with highly hydrophilic monomers, a hydrophilic volatile cosolvent, such as ethanol, ethanol/water, isopropanol, or isopropanol/water, or N,N-dimethylacetamide, may be incorporated with the volatile siloxane or volatile alkane solvent. For relatively insoluble ionic monomers, it may be particularly useful to incorporate N,N-dimethylacetamide. For example, the co-solvent can be present at a concentration of 10 wt-% or less of the total solvent, or 7 wt-% or less, or 5 wt-% or less, or 3 wt-% or less, or 1 wt-% or less, or 0.5 wt-% or less. The co-solvent can be present at a concentration of at least 0.01 wt-% of the total solvent.

Typical addition polymerizable non-siloxy crosslinking agents that are useful in preparing crosslinked polymers can include, but are not limited to, ethylene glycol dimethacrylate, ethylene glycol diacrylate, diethylene glycol dimethacrylate, triethylene glycol dimethacrylate, tetraethylene glycol dimethacrylate, poly(ethylene glycol) dimethacrylate, trimethylolpropane trimethacrylate, N,N-methylenebis(acrylamide), trimethylolpropane triacrylate, diallyl phthalate, triallyl cyanurate, N,N'-(1,2-dihydroxyethylene)bisacrylamide, 1,4-bis(acryloyl)piperazine, glycerol dimethacrylate, 1,3-butanediol dimethacrylate, 1,4-butanediol dimethacrylate, 1,6-hexanediol dimethacrylate, 4,4'-isopropylidenediphenol dimethacrylate, bisphenol A dimethacrylate, divinylbenzene, divinylsulfone, 1,14-tetradecanediol dimethacrylate, polybutadiene dimethacrylate, diurethane dimethacrylate, bisphenol A ethoxylate dimethacrylate, neopentyl glycol diacrylate, neopentyl glycol dimethacrylate, polypropylene glycol) dimethacrylate, and bis(2-methacryloyl)oxyethyl disulfide. Such addition polymerizable crosslinking monomers are not preferred in copolymerization with addition polymerizable siloxysilane monomers in concentrations where the total crosslinking content is greater than 1 weight % to form soluble sacrificial liquid adhesive bandages.

Typical addition polymerizable siloxy crosslinking agents include 1,3-bis(methacryloyloxymethyl)-1,1,3,3-tetramethyldisiloxane, 1,3-bis(3-acrylamidopropyl)tetramethyldisiloxane, 1,3-bis(methacrylamidopropyl)tetramethyldisiloxane, α,ω-bis(methacryloyoxyalkyl)polydimethylsiloxanes, 1,3-bis(3-methacryloyloxypropyl)-1,1,3,3-tetrakis(trimethylsiloxy)disiloxane (TRIS dimer, abbreviated TRIS-D), 1,3-bis(3-methacryloxypropyl)tetramethyldisiloxane, 1,3-bis(3-methacryloxy-2-hydroxypropoxypropyl)tetramethyldisiloxane, 1,3-bis(methacryloyloxypropyl)-1-methacryloyloxypropylbis(trimethylsiloxy)siloxy-1,1,3-tris(trimethylsiloxy)disiloxane (TRIS trimer, abbreviated TRIS-T), 1,1,1,3,3,3-hexakis(methacryloyloxymethyl)disiloxane, 1,2,3,4,5,6-hexakis(methacryloyloxymethyl)benzene, tris(3-methacryloyloxypropyl)trimethylsiloxysilane, tetrakis(3-methacryloyloxypropyl)silane, 1,3-bis[4-vinyloxycarbonyloxy)but-1-yl]tetramethyldisiloxane, and the like. Of the siloxysilane crosslinking monomers, 1,3-bis(3-methacryloyloxypropyl)-1,1,3,3-tetrakis(trimethylsiloxy)disiloxane (TRIS-D), methacryloyloxypropylbis[methacryloyloxypropyldi(trimethylsiloxy)]siloxysilane (TRIS-T), α,ω-bis(methacryloyoxyalkyl)polydimethylsiloxanes, and (methacryloxypropyl)methylsiloxane-dimethylsiloxane copolymer are preferred, with TRIS-D and α,ω-bis(methacryloyoxyalkyl) polydimethylsiloxanes being more preferred, and TRIS-D being most preferred. The polymerizable siloxy crosslinking agents can be present in an amount ranging from 1 to 16 wt-%, or from 2 to 10 wt-%, or from 3-8 wt-%, or from 4-7 wt-%, based on the total weight of the crosslinked siloxysilane polymer.

The crosslinked siloxysilane polymers can either be crosslinked polymers of siloxysilane monomers alone, or crosslinked polymers of siloxysilane monomers with other classes of vinyl-polymerizable comonomers. Most preferably, the siloxysilane monomer is derived from a homopolymer whose glass transition temperature is below 0° C. Most preferably, the siloxysilane monomer is TRIS. Preferably, the crosslinked siloxysilane polymer incorporates a hydrophobic monomer, and more preferably a hydrophobic monomer whose homopolymer is a rigid, transparent, thermoplastic. Most preferably, the added rigid comonomer is methyl methacrylate. The preferred crosslinking agent is a di-, tri-, or multifunctional vinyl polymerizable siloxane or siloxysilane, e.g., TRIS-D. Some other exemplary crosslinked siloxysilane polymers include hydrophobic monomers, preferably hydrophobic monomers whose homopolymers form rigid, transparent, thermoplastics.

For polymerizations with siloxysilane monomers, it is preferable to utilize siloxysilane dimers as crosslinking agents because of their greater solubility and compatibility in a volatile siloxane solvent such as hexamethyldisiloxane. For crosslinking polymerization of the TRIS monomer, the preferred crosslinking agent is TRIS dimer, at a preferred crosslinking concentration ranging from greater than 1 weight % to 16 weight %, or 2 to 10 wt-%, or 3 to 8 wt-% or 4-7 wt-% of the total monomer concentration in the polymer. Certain of these formulations can also include TRIS trimer in the TRIS dimer at concentrations of up to 1.1 wt-%, or up to 0.5 wt-%, or up to 0.3 weight % based on the total monomer concentration. The TRIS trimer can be present in an amount of at least 0.05 wt-%, or at least 0.1 wt-% or at least 0.15 wt-%.

TRIS monomers useful herein can be obtained commercially, e.g., from Silar Laboratories, Wilmington, N.C. Two TRIS monomers with different TRIS dimer contents were utilized, TRIS containing 0.3 weight % TRIS-D and TRIS containing 9.3 weight % TRIS-D and 1.1 weight % TRIS-T. Additionally, TRIS-D was obtained from Gelest Inc., Morrisville, Pa. and added in different proportions to TRIS monomer containing 0.3 weight % TRIS-D.

For the initiation of polymerization, free radical initiators can be used in forming the polymers, including azobisisobutyronitrile, 2,2'-azobis(2,4-dimethylpentanenitrile), 2,2'-azobis-(2-methylbutanenitrile), 2,2'-azodi(2-methylbutyronitrile), 2,2'-azobis(2-methylpropionitrile), 2,2'-azodi(2,4-dimethylvaleronitrile), 2,2'-azobisamidinopropane dihydrochloride, 2,2'-azobis(2-methylpropionamidine) dihydrochloride, 2,2'-azobis(N,N'-dimethylene isobutyramidine) dihydrochloride, 2,2'-azobis(4-methoxy-2,4-dimethyl valeronitrile), 4,4'-azobis(4-cyanovaleric acid), potassium persulfate, ammonium persulfate, benzoyl peroxide, 2,5-dimethyl-2,5-bis(2-ethylhexanoylperoxy)hexane, acetyl peroxide, cumyl peroxide, t-butyl peroxide, t-butyl hydroperoxide, redox initiators and the like. The polymerization can be carried out by solution, emulsion, suspension or precipitation techniques. In addition to thermal initiation, polymerization can also be initiated by oxidation-reduction (redox initiators), uv or visible light photoinitiators, gamma-ray irradiation, sonic irradiation, or controlled (living radical) polymerization initiators.

If crosslinked block, graft, or star siloxy-polymers are desired, these can preferentially be prepared using known techniques, which include, but are not limited to, Atom Transfer Radical Polymerization (ATRP), Reversible Addition-Fragmentation Chain Transfer Polymerization (RAFT), Stable Free Radical Polymerization (SFRP), and Nitroxide-Mediated Radical Polymerization.

The volatile solvent for the crosslinked siloxane-containing polymer is preferably a linear siloxane or a cyclic siloxane, such as hexamethyldisiloxane (HDMS), octamethylcyclotetrasiloxane, decamethylcyclopentasiloxane, and octamethyltrisiloxane, or a linear, branched or cyclic alkane, such as propane, isobutane, liquid butane (e.g., under pressure), pentane, hexane, heptane, octane, isooctane, petroleum distillates, cyclohexane, fluorocarbons, such as trichloromonofluoromethane, dichlorodifluoromethane, dichlorotetrafluoroethane, tetrafluoroethane, heptafluoropropane, 1,1-difluoroethane, pentafluoropropane, perfluoroheptane, perfluoromethylcyclohexane, 1,1,1,2,-tetrafluoroethane, 1,1,1,2,3,3,3-heptafluoropropane, chlorofluorocarbons, in addition to liquid carbon dioxide, and combinations thereof. As used herein, "volatile" has its standard meaning, that is, it can evaporate rapidly at normal temperatures and pressure. For example, a solvent can be volatile if one metric drop (1/20 mL, 50 µL) of the solvent will evaporate completely between 20-25° C. within 5 minutes, or within 4 minutes, or within 3 minutes, or within 2 minutes, or within 1 minute, or within 30 sec, or within 15 sec.

Additionally, an adhesion promoter can be added to the coating polymer mixed with the volatile solvent. Adhesion promoters generally function by increasing creep (flow) and tack (stickiness) of a polymer system. Preferably, the coatings of the present invention exhibit low tackiness. The preferred adhesion promoters include sucrose acetate isobutyrate and low molecular weight fluid polymers of phenyl-containing polysiloxanes, in particular phenyltrimethicone (Dow Corning® 556 Cosmetic Grade Fluid), with phenyltrimethicone being most preferred.

If biocidal properties are desired for the polymer coating, anti-infective agents, such as nano-silver particles, silver sulfadiazine, biguanide salts such as chlorhexidine digluconate, alexidine dihydrochloride, or poly(hexamethylene biguanide) hydrochloride, can be added as suspended solids to the coating polymer in the volatile solvent, as well as solid topical antibiotics such as neomycin, polymyxin B, and bacitracin. Other solid biologically active materials, such as anti-itch agents, such as chamomile, eucalyptus, camphor, menthol, zinc oxide, talc, and calamine, anti-inflammatory agents, such as corticosteroids, antifungal agents, such as terbinafine hydrochloride and miconazole nitrate, and non-steriodal anti-inflammatory agents, such as ibuprofen, can be added in like fashion. Essential oils can also be added as flavoring agents, aromatic agents, or antimicrobial agents, including thymol, menthol, sandalwood, cinnamon, jasmine, lavender, pine, lemon, rose, eucalyptus, clove, orange, mint, spearmint, peppermint, lemongrass, bergamot, citronella, cypress, nutmeg, spruce, tea tree, wintergreen, vanilla, and the like. After evaporation of the volatile, solvent, the polymer coating will contain entrapped active biological or pharmaceutical ingredients for controlled release to a biological surface.

Other Uses and Advantages

The lightly adhesive liquid coating materials of this invention may be useful for protecting or treating skin, nails and mucous membranes, e.g., rashes, skin cuts, abrasions, bed sores, incisions, blisters, poison ivy irritation, mosquito bites, eczema, hives, dry cracked skin, abraded gums and other oral surfaces, hemorrhoids and abraded body areas, inflamed skin and scar tissue, athletes foot, jock itch, herpes infections and, other mucosal membrane incisions and wounds. The crosslinked coating material is useful on surface areas exposed to high levels of movement, e.g., knuckles, knees, elbows, feet and the like. A lightly adherent coating is capable of being pulled away from a surface to which it is applied without causing rupture or tearing of the surface. For biological surfaces such as skin, without removing portions of the epidermis or damaging skin, scars or tissue underneath the lightly adherent coating.

Because the sacrificial coating is non-stinging and rapidly covers exposed nerve endings, pain is reduced immediately. For damaged skin and mucosal surfaces, healing appears to occur more quickly compared to healing in the absence of the liquid bandage. This may be due to the enhanced oxygen permeability of the film and its ability to transmit water vapor, as well as its ability to prevent microbial contamination.

Body adherent medical devices may be coated with the inventive coating materials. Examples of body-adherent medical devices to which the inventive coating materials may be applied include, but are not limited to, bandages, patches, foams, and wound dressings, as well as medical devices used for procedures such as colostomies, ileostomies, Kock ileostomies, enterostomies and jejunostomies.

Still other medical uses include forming films for use in eliminating chapped lips, cold sores, treating internal body surfaces, and providing protection to skin and other surfaces that may be medicated prior to application.

The sacrificial coatings of this invention could be used for applications other than medical body care. For instance, the lightly adherent coating could be used (i) as a coating under labels such that the labels can be removed from an article without leaving adhesive or a portion of the label when the label is removed, (ii) as a sacrificial coating under painters tape to give sharp paint lines with ease removal of the painters tape without paint stripping or stain removal, (iii) as an oxygen or water vapor permeable membrane, or (iv) as an easily removed antimicrobial coating on surfaces such as tables and floors. The coating incorporating a suspended mildewcide could be used to protect grout in tile surfaces. The coating could be used as a water vapor permeable film to protect plants and flowers from dehydrating or to protect them from disease. The coating could also lightly adhere paper together, with easy removal of bound pieces. Further, dried films containing hydrophobic and hydrophilic monomers can be used to prevent fog from forming on surfaces, such as windshield glass or snorkel masks. Additionally, the liquid adhesive coating is further useful as a sunscreen with the incorporation of UV absorbers It should be understood that the coating itself comprises the crosslinked solixy-containing polymer and additives, but not the solvent system, which evaporates once the liquid, polymer-containing coating material is applied to a surface.

The following examples are offered by way of illustration, not by way of limitation. While specific examples have been provided, the above description is illustrative and not restrictive. In the present invention, any one or more of the features of the previously described embodiments can be combined in any manner with one or more features of any other embodiments. Furthermore, many variations of the invention will become apparent to those skilled in the art upon review of the specification. The scope of the invention should, therefore, be determined not with reference to the description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The following examples serve to illustrate the invention without limiting it thereby. It will be understood that variations and modifications can be made without departing from the spirit and scope of the invention.

The monomers, crosslinking agents and solvents used in these examples include:
TRIS (containing 0.3% TRIS-D): 3-methacryloxypropyltris (trimethylsiloxy)silane, Silar Laboratories, Lot #0121708 and Lot #042170, (no trimer reported in either sample).
TRIS (containing 9.3% TRIS-D and 1.1% TRIS-T): Silar Laboratories, Lot #112210NTL.
TRIS dimer (TRIS-D): 1,3-bis(3-methacryloxypropyl)-1,1,3,3-tetrakis(trimethylsiloxy)disiloxane, Gelest, Inc., Lot #2E-18243, 90% purity.
MMA: methyl methacrylate, Alfa Aesar, Lot #15955.
IOA: isooctyl acrylate, Sartomer, Lot #KTE0774.
NIPAM: N-isopropylacrylamide, Jarchem, Lot #N60206
EGDMA: ethylene glycol dimethacrylate, Sartomer, Lot #KTB0237.
SR350: trimethylolpropane trimethacrylate, Sartomer, Lot #VHL5473.
CN301: polybutadiene dimethacrylate, Sartomer, Lot #JJH7507.
RMS-033: 2-4 mole % (methacryloxypropyl)methylsiloxane-96-98 mol % dimethylsiloxane copolymer, Gelest, lot #2H-18870.
DMS-R11: bis(methacryloxypropyl-terminated) polydimethylsiloxane, mol. wt. 900-1200, Gelest, Lot #2K-19482.
VAZO 67: 2,2'-azodi(2-methylbutyronitrile), DuPont, Lot #80224368.
VAZO 52: 2,2'-azodi(2,4-dimethylvaleronitrile), DuPont, Lot #100119418.
Ethyl acetate: VWR, Lot #080910E.
HMDS: hexamethyldisiloxane, Dow Corning, Lot #0004990331.
Isooctane: VWR, Lot #022009A.
Methanol: VWR, Lot #073008A.
DMI: dimethyl itaconate: Sigma Aldrich, Lot #MKBC2742V.
DBI: di-n-butyl itaconate: Sigma Aldrich, Lot #MKBC5067.
OMTS: octamethyltrisiloxane, Dow Corning, Lot #0001903485.
Heptane: Alfa Aesar, Lot #K12T028.

All monomers, solvents, and initiators were used as received. For TRIS-D, the dimer concentration in all Tables was based upon 90% purity, with the remaining 10% being TRIS monomer.

Example 1

Synthesis Procedure for Crosslinked Polymer of TRIS Containing 0.3 Wt % TRIS-D

To 85.12 g of TRIS (containing 0.3 weight % TRIS-D) weighed into a 1 L beaker was added 0.6380 g of Vazo® 67. To this, 320 g of ethyl acetate was added. The mixture was stirred until all components were completely dissolved, and the solution was transferred into a three-neck resin kettle equipped with a nitrogen inlet, thermometer, and a condenser. The kettle was heated with a heating mantle where the polymerization temperature rose to 80° C. It was held at this temperature for about 1 h then decreased slowly to 67° C. over about 35 min. The polymerization was allowed to run for a total of 6 h. Then, 0.2128 g of Vazo® 52 was weighed, diluted with ethyl acetate and added to the reaction. The resin kettle was gently shaken and the temperature increased to 75° C. The polymerization was allowed to continue at this temperature for another 3 h. The solvent was evaporated at room temperature until the volume of the solution was about 10% of the original. The solution was poured into 1 L of methanol and allowed to sit for 24 h in order to precipitate the polymer. The mother liquor was decanted and 300 mL of methanol was added. The mixture was shaken on a shaker for 2 h at room temperature (20-25° C.) and then allowed to sit still for 3 h at room temperature (20-25° C.). The polymer was isolated and the methanol was changed and the washing process was repeated. The polymer was washed in this manner a total of five times. In the methanol mixture the polymer was insoluble but swollen. The polymer, of composition 99.7 wt-% TRIS and 0.3 wt-% TRIS-D (Table 1), was dried under a lamp at about 45° C. for 8 days.

Example 2

Representative Synthesis of Crosslinked Polymers of TRIS (Containing 0.3 wt % TRIS-D) Plus added TRIS-D A 25 mL Schott Duran® glass bottle was charged with 0.4868 g (0.64 mmol) of TRIS-D (1,3-bis(3-methacryloxypropyl)tetrakis(trimethylsiloxy)disiloxane; technical grade, 90% purity; Gelest, lot #2E-18243; [CAS #80722-63-0]). To this, 2.5128 g (5.9 mmol) of TRIS (3-methacryloxypropyltris (trimethylsiloxy)silane, 99.7% purity; Silar Labs, lot #042710; [CAS #17096-07-0]) was added. This was followed by the addition of 4.0234 g of hexamethyldisiloxane, Dow Corning, lot #0004990331; [CAS #107-46-0]. Next, a second 25 mL Schott Duran glass bottle was charged with 0.1554 g of 2,2'-azodi(2-methylbutyronitrile) (Vazo® 67) initiator, [CAS#13472-08-7]. This was followed by the addition of 20.0001 g of hexamethyldisiloxane. The bottle was sealed and shaken until the Vazo™ 67 dissolved. To the bottle previously charged with monomer 3.0009 g of this stock solution was added, delivering 0.0233 g (0.12 mmol) of initiator.

The combined solution was then purged with nitrogen for 5 min before being sealed and placed in an oil bath equilibrated at 70° C. The reaction was allowed to proceed for six hours before being removed from the oil bath and cooled to room temperature. The cap was then removed and the bottle allowed to sit overnight.

The homogeneous reaction solution was then poured as a fine stream into 150 mL of vigorously agitated methanol. This immediately resulted in a globular, opalescent precipitate. The polymer and methanol were placed on a shaker and agitated for 3 h. The methanol was then decanted and 50 mL of fresh methanol added. The agitation was continued for an additional 3 h. This procedure was repeated for a total of three 50 mL washings over a period of 9 h. For the 4$^{th}$ and final wash, the polymer was allowed to sit in 50 mL of un-agitated methanol for 16 h (overnight). The polymers were then dried for 3 days under reduced pressure (aspirator). The yield was 2.7386 g of optically transparent, colorless polymer.

Both TRIS and TRIS-D are believed to have the same radical reactivity because of the similarity of their polymerizable structures, possibly leading to crosslinked polymers that are random in structure. This behavior would facilitate the copolymerization of TRIS and TRIS-D.

The solubility/gel behavior of these polymers is also given in Table 1. Solubility of the purified polymer in HMDS is denoted by either a yes or no, with yes indicating a fluid solution and with no indicating that gel formation occurred. In this Table, the polymer loadings were at 10 wt (weight) % polymer. Solubility, noted by flowable solutions, was found for polymerizations of TRIS and TRIS-D at crosslinking concentrations up to 16.0 wt-%, with gelation being noted at 18.0 wt-%. No gel particles or precipitate were present in the soluble solutions and films cast from these solutions were transparent and smooth. These results are highly surprising in that fluid solutions could be maintained at very high levels of added crosslinking agent.

TABLE 1

Polymers of TRIS Crosslinked with TRIS-D

| TRIS wt-% | TRIS-D wt-% | Solubility in HMDS |
|---|---|---|
| 99.7 | 0.3 | yes, fluid |
| 98.0 | 2.0 | yes, fluid |
| 95.9 | 4.1 | yes, fluid |
| 95.0 | 5.0 | yes, fluid |
| 94.0 | 6.0 | yes, fluid |
| 93.0 | 7.0 | yes, fluid |
| 92.0 | 8.0 | yes, fluid |
| 91.0 | 9.0 | yes, fluid |
| 88.0 | 12.0 | yes, fluid |
| 85.0 | 15.0 | yes, fluid |
| 84.0 | 16.0 | yes, fluid |
| 82.0 | 18.0 | no, gel formation |
| 80.0 | 20.0 | no, gel formation |
| 78.0 | 22.0 | no, gel formation |

Dried polymer films containing from 4.1 to 8.0 wt % TRIS-D were elastic.

Example 3

Synthesis Procedures for TRIS (Containing 0.3 wt % TRIS-D)/MMA Plus Added TRIS-D and TRIS (Containing 9.3 wt % TRIS-D and 1.1 wt % TRIS-T)/MMA For samples with only TRIS-D, similar procedures to that of Example 2 were followed, except that different levels of TRIS-D were added to TRIS, which contained 0.3 wt % TRIS-D, as well as MMA. Polymerizations were conducted in HMDS solvent in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Concentration of monomers used are given in Table 2.

For samples with both TRIS-D and TRIS-T, similar procedures to that of Example 2, except that different levels of TRIS-D were added to TRIS, which contained 0.3 wt % TRIS-D, and TRIS, which contained 9.3% TRIS-D and 1.1% TRIS-T, as well as MMA, and polymerizations were conducted in HMDS solvent in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Concentration of monomers used are given in Table 2.

In this investigation the solubilities of TRIS copolymers with MMA, crosslinked by TRIS-D and some samples also with TRIS-T, are reported in Table 2. The TRIS dimer was either in the TRIS monomer at a dimer concentration of 0.3 wt % or 9.3 wt %, or added as a separate monomer at concentrations up to 5.6 wt %. For the TRIS sample containing TRIS-D at 9.3 wt %, 1.1 additional wt % was TRIS-T, with a final TRIS-T content of 0.2 and 0.3 wt % in the crosslinked polymer. Solubility at 10 wt-% in HMDS, isooctane, octane, and octamethyltrisiloxane was determined from isolated and purified polymers placed in these solvents. It is seen that polymers containing up to a total crosslinking content of 5.6 wt %, solubility was maintained in hexamethyldisiloxane, isooctane, heptane, and octamethyltrisiloxane. The tack to attachment to a finger was minimal in all cases, indicating low adhesive strength to a biological surface.

The tack is associated with the adhesive strength of the coating, wherein a high tack indicates a highly adhesive coating and a low tack indicates a lightly adhesive coating. The latter being preferred for a sacrificial coating. The tack of the polymers prepared in this investigation were evaluated using a scale of 0 to 5, where a value of 5 was for a coating previously applied to a first surface that adhered to a finger and did not fall off when the finger was raised from the coating and the coating had to be removed by another hand or by shaking. On the other hand, a value of 0 for the coating was when the coating fell of the finger as the finger was raised from the coating.

Additionally, it is important to note that these crosslinking polymerizations were conducted at a concentration of 30 weight-% monomer, yet even at these high levels of monomer and crosslinker, it was still possible to produce soluble polymers using these polymerizations.

TABLE 2

TRIS/MMA Polymers Crosslinked with TRIS-D and with TRIS-T

| wt-% Polymer TRIS/MMA/TRIS-D/TRIS-T | Total wt-% Crosslinking Monomers | Solubility HMDS | Solubility Isooctane | Solubility Octane | Solubility OMTS | Tack* |
|---|---|---|---|---|---|---|
| 88.2/9.8/2.0/0 | 1.9 | yes | yes | yes | yes | 1 |
| 78.5/19.6/1.9/0 | 1.9 | yes | yes | yes | yes | 0 |
| 86.5/9.6/3.9/0 | 3.9 | yes | yes | yes | yes | 1 |
| 76.9/19.2/3.9/0 | 3.9 | yes | yes | yes | yes | 0 |
| 75.5/18.9/5.6/0 | 5.6 | yes | yes | yes | yes | 0 |
| 75.2/20.0/4.8/0 | 4.8 | yes | yes | yes | yes | 0 |
| 60.9/35.0/4.1/0 | 4.1 | yes | yes | yes | yes | 0 |
| 76.7/20.0/3.0/0.3 | 3.3 | yes | yes | yes | yes | 0 |
| 77.8/20.0/2.0/0.2 | 2.2 | yes | yes | yes | yes | 0 |

*0-5 scale, with 5 being the most tacky and adherent to a finger.

Example 4

Typical Synthesis Procedure for Polymers of TRIS (with 0.3 wt % TRIS-D)/MMA/IOA, with Added TRIS-D Similar procedures to that of Example 2, except that different levels of TRIS-D were added to TRIS, which contained 0.3 wt % TRIS-D, as well as MMA and IOA, and polymerizations were conducted in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Concentration of monomers used are given in Table 3.

Solubility at 10 wt-% in HMDS, isooctane, octane, and octamethyltrisiloxane was determined from isolated and purified polymers placed in these solvents. From the results of TRIS-D crosslinking of a monomer mixture of TRIS, MMA, and IOA (Table 3), for compositions with TRIS-D crosslinking contents up to 3.4 wt %, it is seen that solubility was maintained in hexamethyldisiloxane, isooctane, heptane, and octamethyltrisiloxane. The tack to attachment to a finger was minimal in all cases.

TABLE 3

TRIS/MMA/IOA Polymers Crosslinked with TRIS-D

| wt-% Polymer TRIS/MMA/IOA/TRIS-D | Total wt-% Crosslinking monomer | Solubility HMDS | Solubility Isooctane | Solubility octane | Tack* |
|---|---|---|---|---|---|
| 52.7/38.4/8.0/0.9 | 0.9 | yes | yes | yes | 0 |
| 52.4/38.0/7.9/1.7 | 1.7 | yes | yes | yes | 0 |
| 52.1/37.6/7.7/2.6 | 2.6 | yes | yes | yes | 0 |
| 51.7/37.3/7.6/3.4 | 3.4 | yes | yes | yes | 0 |

*0-5 scale, with 5 being the most tacky and adherent to a finger.

Example 5

Typical Synthesis Procedure for Crosslinked Polymers of TRIS (with 0.3 wt % TRIS-D) and DMI Plus TRIS-D Similar procedures to that of Example 3 were followed, except that different levels of TRIS-D were added to TRIS, which contained 0.3 wt % TRIS-D, as well as DMI, and polymerizations were conducted in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Concentration of monomers used are given in Table 4. Solubility in HMDS, isooctane, octane, and octamethyltrisiloxane was determined from isolated and purified polymers placed in these solvents.

The results of TRIS-D crosslinking of TRIS with DMI (Table 4) appear to be similar to those of TRIS with MMA, crosslinked with TRIS-D (Table 2). It is seen that for compositions with TRIS-D crosslinking contents up to 6.2 wt %, solubility was maintained in hexamethyldisiloxane, isooctane, heptane, and octamethyltrisiloxane. The tack to a finger was minimal in all cases.

TABLE 4

TRIS/DMI Copolymers Crosslinked with TRIS-D

| wt % Polymer TRIS/DMI/TRIS-D | Total wt-% crosslinking monomer | Solubility HMDS | Solubility isooctane | Solubility octane | Solubility OMTS | Tack* |
|---|---|---|---|---|---|---|
| 79.3/19.7/1.0 | 1.0 | yes | yes | yes | yes | 0 |
| 77.5/19.7/2.8 | 2.8 | yes | yes | yes | yes | 0 |
| 75.4/18.4/6.2 | 6.2 | yes | yes | yes | yes | 0 |

*0-5 scale, with 5 being the most tacky and adherent to a finger.

Example 6

Typical Synthesis Procedure for Crosslinked Polymers of TRIS and DBI Plus TRIS-D Similar procedures to that of Example 3 were followed, except that different levels of TRIS-D were added to TRIS, which contained 0.3 wt % TRIS-D, and DBI, and polymerizations were conducted in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. The concentrations of monomers used are given in Table 5. Solubility in HMDS, isooctane, octane, and octamethyltrisiloxane was determined using isolated and purified polymers placed in these solvents.

From Table 5 it is seen that the solubility behavior of the TRIS/DBI copolymers crosslinked with TRIS-D is similar to that of TRIS/DMI (Table 4) and TRIS/MMA crosslinked with TRIS-D, although the TRIS/DMI cast films from HMDS were slightly more tacky.

TABLE 5

TRIS/DBI Copolymers Crosslinked with TRIS-D

| wt-% Polymer TRIS/DBI/TRIS-D | Total wt-% crosslinking monomer | Solubility HMDS | Solubility isooctane | Solubility octane | Solubility OMTS | Tack* |
|---|---|---|---|---|---|---|
| 79.3/19.7/1.0 | 1.0 | yes | yes | yes | yes | 1 |
| 77.4/19.2/3.4 | 3.4 | yes | yes | yes | yes | 0.5 |
| 75.3/18.5/6.2 | 6.2 | yes | yes | yes | yes | 0.5 |

*0-5 scale, with 5 being the most tacky and adherent to a finger.

Example 7

Synthesis of TRIS (Containing 0.3 Wt % TRIS-D)/MMA Copolymers Crosslinked with Di- and Multi-Functional Polysiloxane Crosslinking Agents Similar procedures to those of Example 3 were used, except that difunctional (DMS-R11) and multifunctional (RMS-033) polysiloxanes were added to TRIS, which contained 0.3 wt % TRIS-D, and MMA, and polymerizations were conducted in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Solubility in HMDS, isooctane, octane, and octamethyltrisiloxane was determined from isolated and purified polymers placed in these solvents. Concentration of monomers used are given in Table 6.

In order to demonstrate that siloxysilane monomers such as TRIS can be crosslinked by difunctional and/or multifunctional polysiloxanes with TRIS-D at combined crosslinking concentrations greater than 1 wt %, TRIS (containing 0.3 wt % TRIS-D) copolymerized with MMA was crosslinked with either dimethacrylate-terminated polydimethylsiloxane (DMS-R11), molecular weight 900-1200 (estimated degree of polymerization=10 dimethylsiloxane units) (Gelest Inc.), or with polydimethylsiloxanes containing 2-4 mole % (methacryloxypropyl)methylsiloxane groups along the polymer main chain (RMS-033), (Gelest Inc.), wherein the methacrylate groups were pendent to the polymer chain (Table 6). It is seen that for both polysiloxane crosslinking agents, solubility was still maintained at a total crosslinking concentration (TRIS-D plus polysiloxane crosslinker) of 2.0 wt %.

TABLE 6

TRIS/MMA Polymers with Polysiloxane Crosslinking Agents

| wt % Polymer | Total wt-% crosslinking monomers | Solubility HMDS | Solubility isooctane | Solubility OMTS | Tack* |
|---|---|---|---|---|---|
| TRIS/MMA/ TRIS-D/RMS-033 78.4/19.6/1.8/0.2 | 2.0 | yes | yes | yes | 0 |
| TRIS/MMA/ TRIS-D/DMS-R11 78.4/19.6/1.8/0.2 | 2.0 | yes | yes | yes | 0 |

*0-5 scale, with 5 being the most tacky and adherent to a finger.

Example 8

Synthesis of TRIS (Containing TRIS-D)/MMA with Non-Siloxane Crosslinking Agents EGDMA, SR350, and CN301

Similar procedures to those of Example 3 were used, except that difunctional non-siloxane crosslinker EGDMA, trifunctional crosslinker SR350, and difunctional polymeric crosslinker CN301 were added to TRIS containing 0.3 wt % TRIS-D, and MMA were used. Polymerizations were conducted in Schott Duran® bottles at 30% solids in a total solvent of 7 g HMDS with 0.0225 g of Vazo® 67 as initiator. Polymerization reactions were degassed with nitrogen, sealed, and placed in an oil bath for 6 h at 71-72° C. Concentration of monomers used are given in Table 7.

Table 2 ($5^{th}$ row) shows that an 80/20 copolymer of TRIS/MMA crosslinked with up to 5.6 wt-% TRIS-D was soluble in HMDS. For comparison, the crosslinking reaction of the TRIS (containing 0.3 wt-% TRIS-D)/MMA polymerization was conducted with three non-siloxy crosslinking agents, including ethylene glycol dimethacrylate (EDGMA), trimethylolpropane trimethacrylate (SR350), and polybutadiene dimethacrylate (CN301) in HMDS solvent. It was found that with the addition of from 1.2 to 4.1 wt-% of EGDMA, SR350, and CN301, with total crosslinking concentrations (TRIS-D plus non-siloxy crosslinker) up to 4.1 wt-%, all polymers gelled in HMDS solvent, i.e., were not soluble. Only below 1 wt-% total crosslinking were these polymers soluble in HMDS, both during polymerization and after purification in methanol and re-dissolution in 10 wt-% HMDS. The behavior of insolubility above 1 wt-% crosslinker is in marked contrast to that noted in Table 2 for the same copolymers of TRIS/MMA crosslinked with up to 5.6 wt-% TRIS-D, which were soluble in HMDS and the other solvents tested. These results illustrate the surprising invention that a siloxy crosslinking agent is needed for siloxy-based polymers to remain soluble in the non-stinging solvents of volatile siloxanes and volatile hydrocarbons at concentrations greater than 1 wt-%.

TABLE 7

Insolubility of TRIS/MMA Polymers with Non-Siloxane Crosslinking Agents

| Polymer | wt-% | Total wt % crosslinking monomer | Solubility HMDS |
|---|---|---|---|
| TRIS/MMA/TRIS-D/EGDMA | 79.7/19.9/0.2/0.2 | 0.4 | yes, fluid |
| TRIS/MMA/TRIS-D/EGDMA | 79.6/19.7/0.2/0.5 | 0.7 | yes, fluid |
| TRIS/MMA/TRIS-D/EGDMA | 79.0/19.8/0.2/1.0 | 1.2 | no, gel formation |
| TRIS/MMA/TRIS-D/EGDMA | 78.2/19.6/0.2/2.0 | 2.2 | no, gel formation |
| TRIS/MMA/TRIS-D/EGDMA | 76.7/19.2/0.2/3.9 | 4.1 | no, gel formation |
| TRIS/MMA/TRIS-D/SR350 | 79.0/19.8/0.2/1.0 | 1.2 | no, gel formation |
| TRIS/MMA/TRIS-D/SR350 | 78.2/19.6/0.2/2.0 | 2.2 | no, gel formation |
| TRIS/MMA/TRIS-D/SR350 | 76.7/19.2/0.2/3.9 | 4.1 | no, gel formation |
| TRIS/MMA/TRIS-D/CN301 | 79.1/19.8/0.2/1.0 | 1.2 | no, gel formation |
| TRIS/MMA/TRIS-D/CN301 | 78.2/19.6/0.2/2.0 | 2.2 | no, gel formation |
| TRIS/MMA/TRIS-D/CN301 | 76.7/19.2/0.2/3.9 | 4.1 | no, gel formation |

Example 9

Representative Synthesis of TRIS/TRIS-D with NIPAM

A 25 mL Schott Duran® glass bottle was charged with 0.1273 g (0.17 mmol, 90% purity) of TRIS-D. To this, 2.6932 g (6.4 mmol, 99.7% purity) of TRIS was added. This was followed by the addition of 0.1877 g (1.7 mmol, 100% purity) of N-isopropylacrylamide, followed by the addition of 4.0234 g of hexamethyldisiloxane.

Next, a second vessel was charged with 0.2270 g (1.2 mmol, 100% purity) of 2,2'-azodi(2-methylbutyronitrile) (Vazo® 67) initiator. This was followed by the addition of 30.0162 g of hexamethyldisiloxane. The bottle was sealed and shaken until the Vazo® 67 dissolved. To the bottle previously charged with monomer, 3.0025 g of this stock solution were added, delivering 0.0227 g (0.12 mmol) of initiator.

The combined solution was then purged with nitrogen for 5 min before being sealed and placed in an oil bath equilibrated at 70° C. The reaction was allowed to proceed for 6 h before being removed from the oil bath and cooled to room temperature, after which the cap was removed and the bottle allowed to sit overnight.

The homogeneous reaction solution was then poured as a fine stream into 150 mL of vigorously agitated methanol. This immediately resulted in a globular, opalescent precipitate. The polymer and methanol were placed on a shaker and agitated for 3 h. The methanol was then decanted and 50 mL of fresh methanol added. The agitation was continued for an additional 3 h. This procedure was repeated for a total of three 50 mL washings over a period of 9 h. For the 4$^{th}$ and final wash, the polymer was allowed to sit in 50 mL of un-agitated methanol for 16 h (overnight). The polymers were then dried for 3 days under reduced pressure (aspirator). The yield was 2.3639 g of optically transparent, colorless polymer.

In U.S. Pat. No. 7,795,326, amphiphilic copolymers of TRIS and NIPAM were prepared, with TRIS-D crosslinking contents preferably less than 1.0 wt-% of TRIS, more preferably between 0.5-0.8 wt-%, and most preferably between 0-0.15 wt-%. Therefore, with the incorporation of NIPAM monomer, the total crosslinking content was further reduced, and all the TRIS/TRIS-D/NIPAM polymers prepared in U.S. Pat. No. 7,795,326 were soluble in HMDS solution at the low crosslinking contents utilized.

In Table 8 are shown the TRIS/TRIS-D/NIPAM copolymers prepared with TRIS-D crosslinking contents of 3.1 and 4.1 wt-%. Each of these polymers was soluble in HMDS solution after preparation and purification. Whereas Tables 1-7 utilized hydrophobic monomers crosslinked with TRIS-D, the results in Table 8 demonstrate that crosslinked amphiphilic siloxy polymers can also be soluble in a siloxy solvent where the siloxy-containing crosslinking agent concentration is greater than 1 wt-%.

TABLE 8

| TRIS/TRIS-D polymers with NIPAM | | | |
|---|---|---|---|
| TRIS wt % | TRIS-D wt % | NIPAM wt % | Solubility HMDS |
| 90.7 | 6.2 | 3.1 | yes, fluid |
| 89.7 | 6.2 | 4.1 | yes, fluid |

Example 10

Decrease in Tack (Adhesive Strength) with Increased Crosslinking of TRIS/TRIS-D Polymers To demonstrate the utility of crosslinked siloxy-based polymeric liquid bandages as sacrificial coatings, the tack (adhesive strength) was measured on four TRIS/TRIS-D copolymers, ranging in dimer concentration of from 0.3 wt-% to 6 wt-% TRIS-D. The tack was determined using films cast from a 10 wt-% polymer solution in HMDS onto the shiny side of a polypropylene liner of Medifilm 390® and dried. The tack of the polymers were based upon a scale of 0 to 5, where a value of 5 was for a coating that adhered to a finger and did not fall off when the finger was raised from the coating and the coating had to be removed by another hand or by shaking. On the other hand, a value of 0 for the coating was when the coating fell of the finger as the finger was raised from the coating.

Table 9 shows that as the TRIS-D crosslinking concentration increases from 0.3 wt-% to 6.0 wt-%, the tack decreases from a value of 3 to a value of 0.5. Thus, with increasing crosslinking content, the adhesion to a surface decreases, allowing the adhesive polymer film to function as a sacrificial coating when covered by a more tenacious adhesive. Additionally, each of the crosslinked polymers studied remained soft and flexible, a property that is needed to facilitate conformal behavior for a liquid bandage.

TABLE 9

Decreasing tack with increasing crosslinking of TRIS/TRIS-D copolymers

| Polymer, wt-% | Total wt-% cross-linking monomer | Solubility in HMDS | Solubility in Iso-octane, Heptane, and OMTS | Tack (5 is the tackiest) | Film Property |
|---|---|---|---|---|---|
| TRIS/TRIS-D | | | | | |
| 99.7/0.3 | 0.3 | yes | yes | 3 | flexible |
| 98.0/2.0 | 2.0 | yes | yes | 2 | flexible |
| 95.9/4.1 | 4.1 | yes | yes | 1 | flexible |
| 94.0/6.0 | 6.0 | yes | yes | 0.5 | flexible |

Example 11

Sacrificial Coatings

In order to ascertain the effectiveness of the above described crosslinked siloxysilane polymers, delivered to blue dye-treated skin in a hexamethyldisiloxane solvent and evaporated to form a clear film as a sacrificial coating, the following preparations were studied on two human volunteers, wherein the sacrificial coating was first applied to the skin and dried, followed by over-coating with a portion of a commercial ostomy adhesive device according to the following procedure:

Blue food dye was applied onto human arms and abdominal skin of volunteers using a paper towel and allowed to dry for 5 min. The sacrificial coating polymers were dissolved in HMDS to give 5 wt-% solutions. About 0.045 mL of solution for each sample was applied on the abdominal or arm skin of volunteers and allowed to dry for 4 min. A ConvaTec ActiveLife® One-Piece Pouch with Stomahesive® Skin Barrier ostomy system was cut into eight pie-shaped slices and a slice was applied on top of each sacrificial polymer coating, and held by hand with moderate pressure for 2 min. The Stomahesive® Skin Barrier was manually removed after 12 h. An average value of pain of removal of the Stomahesive from the sacrificial coating was determined as well as an average value of the amount of blue food dye removed by the Stomahesive from the skin.

The ConvaTec multi-purpose skin barrier adhesive holds an ostomy pouch in place during wear, while being filled with body fluids. Because this device must be held securely to the skin to prevent leakage of the ostomy fluids, its removal from the body when the pouch is filled may be painful because of stripping of epidermal cells and hair.

Two polymer systems were studied. TRIS (containing 0.3 wt-% TRIS-D) and dimethyl itaconate (Table 4) and TRIS containing TRIS-D and TRIS-T with methyl methacrylate (Table 2) were subject to skin tests as discussed above. Blue food dye was applied on human arms and abdominal skin of volunteers using a paper towel and let dry for 3 min.

For both systems it is seen from Tables 10 and 11 that the polymer with the greater crosslinking content is a more effective sacrificial coating under a pressure sensitive adhesive as the pain of removal is low and more dye remained on the skin, showing that the samples with the greater content of crosslinking are less damaging to the skin when removed by a strongly adherent pressure sensitive adhesive

TABLE 10

Skin tests for crosslinked TRIS/DMI polymers with TRIS-D

| wt-% Polymer TRIS/DMI/TRIS-D | Total wt-% Crosslinking monomer | Pain on removal | Dye remaining on skin |
|---|---|---|---|
| 77.5/19.7/2.8 | 2.8 | moderate | minimal |
| 75.4/18.4/6.2 | 6.2 | slight | moderate |

TABLE 11

Skin tests for TRIS/MMA using low dimer TRIS, high dimer TRIS, and TRIS-T

| wt-% Polymer TRIS/DMI/ TRIS-D/TRIS-T | Total wt-% Crosslinking monomer | Pain on removal | Dye remaining on skin |
|---|---|---|---|
| 77.8/20.0/2.0/0.2 | 2.2 | slight | minimal |
| 76.7/20.0/3.0/0.3 | 3.3 | slight | large |

Example 12

Moisture Vapor Transmission Rate (MVTR) Study for TRIS/TRIS-D Copolymers

Siloxane-based polymers are noted for their high Moisture Vapor Transmission Rates (MVTR's). This property aids in wound healing. Normal unabraded skin loses moisture vapor at an average rate of 200 $g/m^2/day$ in most areas; the palms of the hand and soles of the feet respire at an average of 500 $g/m^2/day$. A MVTR of <35 $g/m^2/hour$ (<840 $g/m^2/day$) is documented as an operational definition of moist wound coating sufficiently effective to speed chronic and acute wound healing. It is reported that dressings with a MVTR above this critical level delay healing (Bolton, L. L., Evidence-based Report Card: Operational definition of moist wound healing, J. Wound Ostomy & Continence Nursing, 2007; 34(1):23-29), most probably caused by dehydration of the wounded area.

In this investigation, the MVTR's were determined by casting a film of the liquid adhesive coating materials on the smooth side of a pre-warmed aluminum block on a Corning hot plate, model PC 400. A rectangular strip of Teflon coated release film was placed over the aluminum block, matte side up prior to casting the film. A strong stream of nitrogen was used to blow off surface particles. The desired polymer solution was degassed by briefly boiling and allowed to cool to room temperature. Next, a 0.25 mL portion of the polymer solution was used to coat the release film in areas similar to that of the diameter of the Schott Duran® bottles. After sitting for 1 min, the aluminum block was rotated by 90° every 15 sec, while blowing on the pooled solution. A gentle stream of nitrogen was then blown across the droplets, and they were rotated 180° every minute. Once the films were dry, they were removed from the hot plate and allowed to come to room temperature. The samples were then sufficiently dry to attach to the bottles.

For affixing the cast films to the water filed Schott Duran® bottles, the polymer films were then removed from the release liner with a long, thin razor blade. The same polymer solution that was used to cast the film was used to place a fine bead of solution around the rim of the bottle and allowed to dry. The fine bead process was repeated three times to ensure an adequate quantity of polymer was available to form a seal. A drop of polymer solution was added around the lip of the Schott Duran® bottle and then let it sit for about 10 to 15 sec. Once tacky, the polymer film from the razor blade was then attached to the neck of the bottle by pressing the free hanging edge onto the lip of the bottle, using the razor to guide the film across the opening. The films can be pressed down with a thumb to get good attachment. Once the films were affixed, nitrogen was flowed gently over the surface of the film to promote evaporation and to discourage excess solvent from compromising the integrity of the film. After 1 h of drying, the weight of each bottle was recorded and then placed into a desiccator filled with Drierite. The desiccator was then placed into the incubator at 37° C. and weight loss measurements were conducted every hour. Polymer film thicknesses were measured with a micrometer and recorded in mils (0.001 inch units).

TABLE 12

MVTR of TRIS/TRIS-D Copolymers

| wt-% Polymer TRIS/TRIS-D | MVTR (g/m²/day) | $R^2$ | Total Time (min) | Film Thickness (mil) +/− 1σ |
|---|---|---|---|---|
| 99.7/0.3 | 748 | 0.9898 | 268 | 3.28 +/− 0.18 |
| 85.0/15.0 | 618 | 0.9968 | 380 | 3.10 +/− 0.12 |

From these data, the MVTR values of crosslinked TRIS copolymer films are consistent with those needed for wound healing, preventing both dehydration of the wounded area and occlusion of body fluids.

Example 13

Industrial Application

To demonstrate the utility of the sacrificial coatings in an industrial environment, an experiment was conducted in preserving cardboard boxes from surface tearing when pressure sensitive tape is removed from the box surface. Utilizing clear packaging tape and a corrugated cardboard box BX7781, 4 G and 4 GV, the packaging tape was pressed on the cardboard box and left for 15 min. The tape was then removed from the box, stripping the top layer of brown fibers from the box. The polymer of 77.8/20.0/2.0/0.2 TRIS/MMA/TRIS-D/TRIS-T (Table 2) in 95 wt-% HMDS was brushed on another location of the cardboard box and dried, followed by pressing tape onto the treated box surface. After 15 min the adherent tape was removed, with no stripping of the top layer of the box.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

We claim:
1. A liquid, polymer-containing coating material comprising:
about 1 to 50 weight % crosslinked siloxy-containing polymer, comprising:
34 to 99 monomer-weight-% of at least one polymerizable siloxy-containing monomer component, and
greater than 1 to 16 monomer-weight-% siloxy-containing crosslinking agent, wherein said monomer-weight-% is based upon total weight of the crosslinked siloxy-containing polymer; and
about 50 to 99 weight % of a non-stinging, volatile, hydrophobic liquid as part of a solvent system, said crosslinked siloxy-containing polymer being solubilized in said solvent system; wherein weight percentages are based on the total weight of the liquid, crosslinked polymer-containing coating material; and wherein said non-stinging, volatile, hydrophobic liquid is selected from the group consisting of volatile linear and cyclic siloxanes, volatile alkanes, volatile fluorocarbons and chlorofluorocarbons, liquid carbon dioxide under pressure, and combinations thereof, wherein said siloxy-containing crosslinking agent comprises a di-, tri- or multifunctional vinyl polymerizable siloxane or siloxysilane.

2. The liquid, polymer-containing coating material according to claim 1, wherein said liquid coating material forms an adherent, conformable, water-insoluble coating when applied to a surface at room temperature.

3. The liquid, polymer-containing coating material according to claim 1, wherein said crosslinked siloxy-containing polymer further comprises a non-siloxy comonomer in an amount between 0 and 50 weight-%.

4. The liquid, polymer-containing coating material according to claim 3, wherein said non-siloxy monomer is selected from the group consisting of methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, stearyl acrylate, stearyl methacrylate, benzyl methacrylate, 2-butoxyethyl acrylate, n-butyl acrylate, n-butyl methacrylate, methacrylic anhydride, 2-(methacryloyloxy)ethyl acetoacetate, ethyl acrylate, behenyl methacrylate, ethyl methacrylate, dimethyl itaconate, di-n-butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, α-methylstyrene, styrene, p-t-butylstyrene, 4-methoxystyrene, N-vinylcarbazole, n-octadecyl acrylate, n-octadecyl methacrylate, 2-phenylethyl methacrylate, n-tridecyl methacrylate, vinyl benzoate, vinyl naphthalene, di-isooctyl itaconate, acrylamide, N-methylacrylamide, N-phenylacrylamide, N-ethylacrylamide, N-(hydroxymethyl)acrylamide, N-(hydroxymethyl)methacrylamide, N-[tris(hydroxymethyl)methylacrylamide, N-isopropylacrylamide, N,N-diethylacrylamide, N,N-dimethylacrylamide, N,N-dimethylmethacrylamide, N-diphenylmethylacrylamide, N-(triphenylmethyl)methacrylamide, N-acryloylaminodoethoxyethanol, diacetone acrylamide, N-vinylpyrrolidone, N-vinylcaprolactam, N-vinylformamide, N-vinyl-N-methylformamide, N-vinylacetamide, N-vinylphthalamide, N-(2-methacryloyloxyethyl)ethylene urea, N-(2-methacrylamidoethyl)ethylene urea, 4-acryloylmorpholine, maleimide, N-methylmaleimide, N-(2,3-dihydroxypropyl)maleimide, N-vinylsuccinimide, N-vinyldiacetamide, epsilon-acryloyllysine, N-acryloyluracil, N-acryloylthymine, N-acryloyladenine, N-acryloylguanine, N-acryloylurea, N-acryloylguanidine, N-acrylglucosamine, N-allylpyrrolidone, N-allylacetamide, N,N-dimethylaminoethyl methacrylate, N,N-dimethylaminoethyl acrylate, N,N-diethylaminoethyl methacrylate, N,N-diethylaminoethyl acrylate, N,N-dimethylaminopropylmethacrylamide, N,N-dimethylaminopropylacrylamide, vinylbenzyl-N,N-dimethylamine, methacryloyloxyethylamine, N-vinylimidazole, 4(5)-vinylimidazole, 4-vinylpyridine, 2-vinylpyridine, 2-methyl-5-vinylpyridine, vinyltriazine, 4-aminostyrene, p-hydroxystyrene, 2-hydroxyethyl methacrylate, 2-hydroxyethyl acrylate, glyceryl methacrylate, glyceryl acrylate, 4-hydroxybutyl acrylate, polyethylene glycol) monoacrylate, poly(ethylene glycol) monomethacrylate, poly(ethylene glycol monomethyl ether) methacrylate, diethylene glycol monoacrylate, diethylene glycol monomethacrylate, triethylene glycol monoacrylate, triethylene glycol monomethacrylate, tetraethylene glycol monoacrylate, tetraethylene glycol monomethacrylate, triethylene glycol methyl ether methacrylate, triphenylmethyl methacrylate, fluorinated monomeric siloxanes, fluorinated itaconates, fluorinated methacrylates or acrylates, acrylic acid, methacrylic acid, itaconic acid, fumaric acid, β-carboxyethyl acrylate, mono-2-(methacryloyloxy)ethyl maleate, mono-2-(methacryloyloxy)ethyl succinate, 2-acetamidoacrylic acid, 2-acrylamidoglycolic acid, 2-acrylamido-2-methyl-1-propanesulfonic acid and its salts, vinylbenzoic acid, (3-acrylamidopropyl)trimethylammonium chloride, [3-(methacryloylamino)propyl]trimethylammonium chloride, (3-methacryloyloxyethyl)trimethylammonium chloride, vinyl benzyltrimethylammonium chloride, and related salts, [3-(methacryloylamino)propyl]dimethyl(3-sulfopropyl)ammonium hydroxide inner salt, [2-(methacryloyloxy)ethyl]dimethyl-(3-sulfopropyl)ammonium hydroxide inner salt and combinations thereof.

5. The liquid, polymer-containing coating material according to claim 1, wherein said polymerizable siloxy-containing monomer is selected from the group consisting of polymerizable alkylsiloxysilanes, alkylarylsiloxysilanes, arylsiloxysilanes or monofunctional polymerizable polysiloxanes and combinations thereof.

6. The liquid, polymer-containing coating material according to claim 1, wherein said polymerizable siloxy-containing monomer is selected from the group consisting of
3-methacryloyloxypropyltris(trimethylsiloxy)silane (TRIS), 3-methacryloyloxypropylpentamethyldisiloxane, 3-methacryloyloxypropylbis(trimethylsiloxy)methylsilane, 3-methacryloyloxypropyltris(vinyldimethylsiloxy)silane, 3-methacryloyloxymethylbis(trimethylsiloxy)(pentamethyldisiloxanyl)silane-, 3-methacryloyloxyethyltris(pentamethyldisiloxanyl)silane, methacryloyloxymethylbis(trimethylsiloxy)methylsilane, methacryloyloxymethyltris(trimethylsiloxy)silane, 3-methacryloyloxypropylheptacyclopentyl-T8-silsesquioxane, 3-methacryloyloxypropylheptaisobutyl-T8-silsesquioxane, 3-acryloyloxypropylmethylbis(trimethylsiloxy)silane, 3-acryloyloxypropyltris(trimethylsiloxy)silane, 3-acryloyloxypropylpentamethyldisiloxane, 3-methacryloyloxypropyl-1,1,1-triphenyl-3,3-dimethyldisiloxane, methylbis(trimethylsiloxy)silylpropylglyceryl methacrylate, tris(trimethylsiloxy)silylpropylglyceryl methacrylate, methacryloyloxymethylphenethyltris(trimethylsiloxy)silane, di[(trimethylsiloxy)silylpropyl] itaconate, 3-methacrylamidopropylbis(trimethylsiloxy)methylsilane, 3-methacrylamidopropyltris(trimethylsiloxy)silane, 3-acrylamidopropyltris(trimethylsiloxy)silane, N-(trimethylsiloxy)silylpropyl maleimide, p-vinylphenyltris(trimethylsiloxy)silane, p-vinylbenzyltris(trimethylsiloxy)silane, vinyloxyethyltris(trimethylsiloxy)silane, vinylnonyldimethyl(trimethylsiloxy)silane, vinylnonyltris(trimethylsiloxy)silane, vinylmethylbis(trimethylsiloxy)silane, vinylpentamethyldisiloxane, O-(vinyloxyethyl)-N-(tris[trimethylsiloxy]silylpropyl)urethane, vinylphenylbis(trimethylsiloxy)silane, vinyltris(dimethylsiloxy)silane, vinyltris(trimethylsiloxy)silane, allyltris(trimethylsiloxy)silane, N-tris(trimethylsiloxysilyl)propylmaleimide, bis(trimethylsiloxy)silylpropyl itaconate, vinyl-terminated polydimethylsiloxane, 3-(trimethylsilyl)propyl vinyl carbonate, 3-[tris(trimethylsiloxy)silyl]propyl vinyl carbonate, 3-[tris(trimethylsiloxy)silyl]propyl vinyl carbamate, t-butyldimethylsiloxyethyl vinyl carbonate, trimethylsilylethyl vinyl carbonate, trimethylsilylmethyl vinyl carbonate, polydimethylsiloxane monoacrylate, polydimethylsiloxane monomethacrylate, polymethylphenylsiloxane monoacrylate, polymethylphenylsiloxane monomethacrylate, monomethacryloxypropyl-terminated polydimethylsiloxanes, 3-acryloyloxypropyltris(polydimethylsiloxanyl)silane, mono(3-acryloxy-2-hydroxypropoxypropyl)-terminated polydimethylsiloxane, O-methacryloxyethyl-N-(trimethylsiloxysilylpropyl)carbamate, O-methacryloxyethoxy-N-[bis(trimethylsiloxy)methylsilyl]propylcarbamate, N-(3-methacryloxy-2-hydroxypropyl)-3-aminopropyltris(trimethylsiloxy)silane, (3-methacryloxy-2-hydroxypropoxy)propylbis(trimethylsiloxy)methylsilane, methacryloyloxy(polyethyleneoxy)propyltris(trimethylsiloxy)silane, and combinations thereof.

7. The liquid, polymer-containing coating material according to claim 1, wherein said polymerizable siloxy-containing monomer comprises 3-methacryloyloxypropyltris(trimethylsiloxy)silane (TRIS).

8. The liquid, polymer-containing coating material according to claim 1, wherein said siloxy-containing crosslinking agent is selected from the group consisting of 1,3-bis(methacryloyloxymethyl)-1,1,3,3-tetramethyldisiloxane, 1,3-bis(3-acrylamidopropyl)tetramethyldisiloxane, 1,3-bis(methacrylamidopropyl)tetramethyldisiloxane, α,ω-bis(methacryloyloxyalkyl)polydimethylsiloxane, 1,3-bis(3-methacryloyloxypropyl)-1,1,3,3-tetrakis(trimethylsiloxy)disiloxane (TRIS dimer), 1,3-bis(3-methacryloxypropyl) tetramethyldisiloxane, 1,3-bis(3-methacryloxy-2-hydroxypropoxypropyl)tetramethyldisiloxane, 1,3-bis(methacryloyloxypropyl)-1-methacryloyloxypropylbis(trimethylsiloxy)siloxy-1,1,3-tris(trimethylsiloxy)disiloxane (TRIS trimer), 1,1,1,3,3,3-hexakis(methacryloyloxymethyl)disiloxane, 1,2,3,4,5,6-hexakis(methacryloyloxymethyl)benzene, tris(3-methacryloyloxypropyl)trimethylsiloxysilane, tetrakis(3-methacryloyloxypropyl)silane, bis(methacryloxypropyl-terminated) polydimethylsiloxanes, (methacryloxypropyl)methylsiloxane-dimethylsiloxane copolymer, 1,3-bis[4-vinyloxycarbonyloxy)but-1-yl]tetramethyldisiloxane, and combinations thereof.

9. The liquid, polymer-containing coating material according to claim 1, wherein said siloxy-containing crosslinking agent is 1,3-bis(3-methacryloyloxypropyl)-1,1,3,3-tetrakis(trimethylsiloxy)disiloxane (TRIS dimer).

10. The liquid, polymer-containing coating material according to claim 1, wherein said volatile solvent comprises at least one of hexamethyldisiloxane, octamethylcyclotetrasiloxane, decamethylcyclopentasiloxane, octamethyltrisiloxane, propane, isobutane, butane (under pressure), pentane, hexane, heptane, octane, isooctane, petroleum distillates, cyclohexane, trichloromonofluoromethane, dichlorodifluoromethane, dichlorotetrafluoroethane, tetrafluoroethane, heptafluoropropane, 1,1-difluoroethane, pentafluoropropane, perfluoroheptane, perfluoromethylcyclohexane, 1,1,1,2,-tetrafluoroethane, 1,1,1,2,3,3,3-heptafluoropropane, and liquid carbon dioxide.

11. The liquid, polymer-containing coating material according to claim 1, wherein said non-stinging, volatile hydrophobic liquid comprises hexamethyldisiloxane.

12. The liquid, polymer-containing coating material according to claim 1, wherein said non-stinging, volatile hydrophobic liquid contains 10% or less of a polar solvent.

13. The liquid, polymer-containing coating material according to claim 1, wherein said siloxy-containing polymer comprises 3-methacryloyloxypropyltris(trimethylsiloxy)silane (TRIS), methyl methacrylate, and 1,3-bis(3-methacryloyloxypropyl)-1,1,3,3-tetrakis(trimethylsiloxy)disiloxane (TRIS dimer).

14. The liquid, polymer-containing coating material according to claim 1, wherein said siloxy-containing polymer comprises 3-methacryloyloxypropyltris(trimethylsiloxy)silane (TRIS), methyl methacrylate, 1,3-bis(3-methacryloyloxypropyl)-1,1,3,3-tetrakis(trimethylsiloxy)disiloxane (TRIS dimer), and 1,3-bis(methacryloyloxypropyl)-1-methacryloyloxypropylbis(trimethylsiloxy)siloxy-1,1,3-tris(trimethylsiloxy)disiloxane (TRIS trimer).

15. The liquid, polymer-containing coating material according to claim 1, wherein said siloxy-containing polymer comprises 3-methacryloyloxypropyltris(trimethylsiloxy)silane (TRIS), methyl methacrylate, isooctyl acrylate and 1,3-bis(3-methacryloyloxypropyl)-1,1,3,3-tetrakis(trimethylsiloxy)disiloxane (TRIS dimer).

16. The liquid, polymer-containing coating material according to claim 1, wherein said siloxy-containing polymer comprises 3-methacryloyloxypropyltris(trimethylsiloxy)silane (TRIS), dimethyl itaconate, and 1,3-bis(3-methacryloyloxypropyl)-1,1,3,3-tetrakis(trimethylsiloxy)disiloxane (TRIS dimer).

17. The liquid, polymer-containing coating material according to claim 1, wherein said siloxy-containing polymer comprises 3-methacryloyloxypropyltris(trimethylsiloxy)silane (TRIS), di-n-butyl itaconate, and 1,3-bis(3-methacryloyloxypropyl)-1,1,3,3-tetrakis(trimethylsiloxy)disiloxane (TRIS dimer).

18. The liquid, polymer-containing coating material according to claim 1, wherein said siloxy-containing polymer comprises 3-methacryloyloxypropyltris(trimethylsiloxy)silane (TRIS), N-isopropylacrylamide, and 1,3-bis(3-methacryloyloxypropyl)-1,1,3,3-tetrakis(trimethylsiloxy)disiloxane (TRIS dimer).

19. The liquid, polymer-containing coating material according to claim 1, wherein said crosslinked siloxy-containing polymer further comprises 0.01 to 50 weight % non-siloxy comonomer, and wherein said crosslinked siloxy-containing polymer is solubilized in said solvent system.

20. A method of coating a surface, comprising applying a liquid, polymer-containing coating material according to claim 1 to a surface in order to form a coating.

21. The method according to claim 20, wherein said surface comprises skin.

22. The method according to claim 20, further comprising applying an adhesive to said coating.

23. The method according to claim 20, further comprising applying a medical device over said coating.

24. The method according to claim 1, wherein said polymer comprises 1.2 to 16 monomer-weight-% siloxy-containing crosslinking agent.

25. A soluble, crosslinked siloxy-containing polymer, comprising:
   34 to 99 monomer-weight-% of at least one polymerizable siloxy-containing monomer component, and
   greater than 1 to 16 monomer-weight-% siloxy-containing crosslinking agent, wherein said monomer-weight-% is based upon total weight of the crosslinked siloxy-containing polymer, wherein a solubility limit of said polymer in HMDS or isooctane is at least 5 wt-%, wherein said siloxy-containing crosslinking agent comprises a di-, tri- or multifunctional vinyl polymerizable siloxane or siloxysilane.

26. The soluble crosslinked siloxy-containing polymer of claim 25, wherein said polymer comprises 1.2 to 16 monomer-weight-% siloxy-containing crosslinking agent.

* * * * *